United States Patent [19]

Sandi-Matamoros

[11] Patent Number: Plant 6,346

[45] Date of Patent: Oct. 18, 1988

[54] DRACAENA MAGENTA

[75] Inventor: Misael Sandi-Matamoros, Limon, Costa Rica

[73] Assignee: Tropical Botanicals Corporation, Medley, Fla.

[21] Appl. No.: 927,223

[22] Filed: Nov. 5, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—John Gibson Semmes

[57] ABSTRACT

A new and distinct variety of Dracaena plant characterized by medium long, narrow, sword shaped dense spreading leaves, the leaves being compactly grouped and nearly erect, the texture thereof being shiny and smooth and the distinctive color of the leaves being on the undersides, a green mid-vein stripe narrowing from base toward apex, surrounded by maroon and the uppersides having a wider green mid-band stripe narrowing from base to apex and blending into maroon.

1 Drawing Sheet

DESCRIPTION

The present invention relates to a new and distinct variety of ornamental plant of the genus Dracaena, originated as a mutation of *Dracaena marginata* (unpatented).

The mutation was discovered in the nursery Matas de Costa Rica, Sequerres Costa Rica. It has been reproduced asexually at the nursery by means of tip cuttings and its distinguishing characteristics remain permanent.

The accompanying photograph shows the new variety in approximately true colors, the plant shown being 24 weeks old and 18" tall from stem to tallest leaf apex at time of photographing.

In the following detailed description of the new variety, the color method chosen for identification has been taken from the Inter-Society Color Council, National Bureau of Standards, Supplement to Circular 553, *The ISCC Method of Designating Color and a Dictionary of Color Names.*

The new variety is a herbaceous plant and has medium long, narrow, sword shaped, dense spreading leaves 6–18" in length. The width of the leaves varies from 3/16–⅞". As in the mother plant, *Dracaena marginata,* the leaves are compactly grouped and slightly pendant. The texture of the leaves is the same as the mother plant.

The habit of growth is similar to the parent plant, growing about 20" the first year if allowed to grow without cutting. Because of the unique color pattern, this variety makes an excellent house plant. It propagates true from cuttings, rooting easily at nodes planted below the soil surface.

Among the outstanding features is the coloration of the leaves. The leaf underside has a green (No. 111 Dark Green) mid-vein stripe ⅜" wide at the base and narrowing toward the apex gradually disappearing approximately halfway between the base and apex, surrounded by maroon (No. 44 Deep Maroon) the upper leaf surface has a wider, less distinct mid-vein band (No. 111 Dark Green) ½" wide narrowing to a point at the apex blending into maroon (No. 44 Dark Maroon).

COMPARISONS

The variety most like my new variety is the *Dracaena marginata,* unpatented. The principal differences between the respective varieties lie in the color pattern of their leaves as follows:

1. The color pattern of the leaves of the new variety consist of:

a more narrow green mid-vein band surrounded by a wider border of maroon.

2. Where the green is predominant in *Dracaena marginata,* there is a greater proportion of maroon in the new variety.

Having thus disclosed my discovery, I claim:

1. The new distinct variety of Dracaena plant substantially as herein shown and described, characterized particularly by medium long, narrow, sword shaped, dense spreading leaves, the leaves being shiny and smooth and the distinctive color pattern of its leaves being, on the underside, a green mid-vein, striped narrowing from base toward apex, surrounded by maroon and the upper leaf side having a wider green mid-band narrowing from base toward apex and blending into maroon.

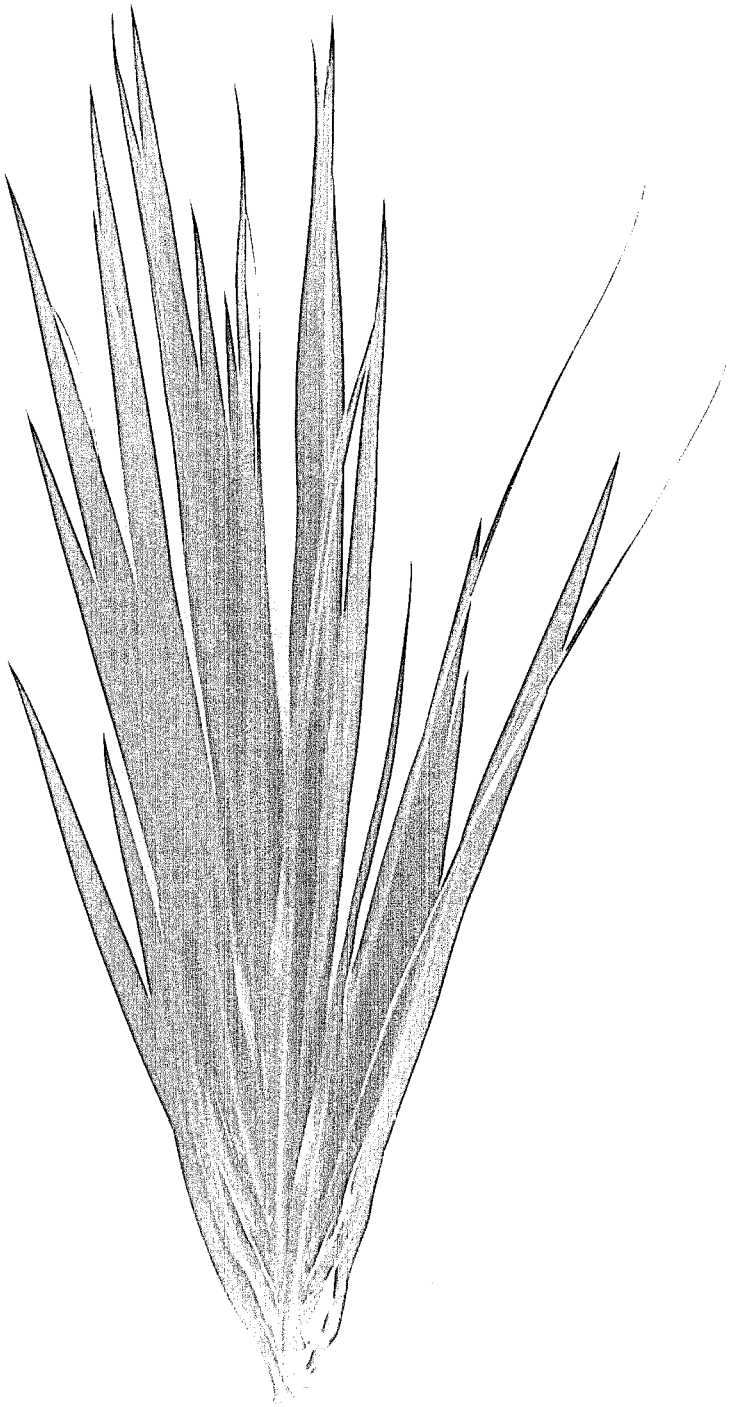

* * * * *